(12) United States Patent
Cunnington et al.

(10) Patent No.: US 11,903,712 B2
(45) Date of Patent: Feb. 20, 2024

(54) PHYSIOLOGICAL STRESS OF A USER OF A VIRTUAL REALITY ENVIRONMENT

(71) Applicant: International Business Machines Corporation, Armonk, NY (US)

(72) Inventors: Daniel T. Cunnington, Winchester (GB); Elizabeth Bowen, Hook (GB); Gwilym B. L. Newton, Winchester (GB); Elizabeth J. Maple, Basingstoke (GB); Graham White, Alton (GB)

(73) Assignee: International Business Machines Corporation, Armonk, NY (US)

( * ) Notice: Subject to any disclaimer, the term of this patent is extended or adjusted under 35 U.S.C. 154(b) by 374 days.

(21) Appl. No.: 16/004,130

(22) Filed: Jun. 8, 2018

(65) Prior Publication Data
US 2019/0374148 A1 Dec. 12, 2019

(51) Int. Cl.
*A61B 5/16* (2006.01)
*G06F 3/01* (2006.01)
*A61B 5/11* (2006.01)
*A61B 5/00* (2006.01)
*G06T 19/00* (2011.01)

(52) U.S. Cl.
CPC ............ *A61B 5/165* (2013.01); *A61B 5/0077* (2013.01); *A61B 5/11* (2013.01); *A61B 5/162* (2013.01); *A61B 5/4803* (2013.01); *A61B 5/4884* (2013.01); *A61B 5/7278* (2013.01); *A61B 5/7445* (2013.01); *G06F 3/011* (2013.01); *G06T 19/006* (2013.01)

(58) Field of Classification Search
None
See application file for complete search history.

(56) References Cited

U.S. PATENT DOCUMENTS 5,376,128 A * 12/1994 Bozeman, Jr. ....... A61B 5/1121
623/24
5,513,129 A * 4/1996 Bolas ..................... G06F 3/011
703/13
5,524,637 A 6/1996 Erickson
(Continued)

FOREIGN PATENT DOCUMENTS

JP 2009213782 A * 9/2009
JP 2009213782 A 9/2009
(Continued)

OTHER PUBLICATIONS

Machine translation of JP 2009213782 A. Retrieved from espacenet. com on Sep. 7, 2022. (Year: 2022).*
(Continued)

*Primary Examiner* — Jacqueline Cheng
*Assistant Examiner* — Samuel C Kim
(74) *Attorney, Agent, or Firm* — Grant Johnson

(57) ABSTRACT

Proposed are concepts of identifying physiological stress of a user of a virtual reality environment by displaying to the user a virtual object at an object location within the virtual reality environment and instructing the user to interact with the displayed virtual object. A measure of physiological stress may then be determined based on a detected parameter of the user's movement in response to the instruction, and the measure of physiological stress may be associated with a part of the user's body based on the object location.

8 Claims, 4 Drawing Sheets

(56) References Cited

U.S. PATENT DOCUMENTS

| | | | | |
|---|---|---|---|---|
| 5,577,981 | A * | 11/1996 | Jarvik | A63B 71/0622 482/4 |
| 5,890,995 | A * | 4/1999 | Bobick | A63B 24/0084 482/4 |
| 6,425,764 | B1 | 7/2002 | Lamson | |
| 7,073,129 | B1 | 7/2006 | Robarts | |
| 7,150,048 | B2 * | 12/2006 | Buckman | A41D 13/0182/465 |
| 8,503,086 | B2 | 8/2013 | French | |
| 2004/0127337 | A1 * | 7/2004 | Nashner | A63B 24/00 482/100 |
| 2009/0124863 | A1 * | 5/2009 | Liu | A61B 5/1128 600/300 |
| 2010/0137748 | A1 * | 6/2010 | Sone | A61B 5/6887 600/595 |
| 2011/0230792 | A1 * | 9/2011 | Sarig-Bahat | A61B 5/1124 600/595 |
| 2011/0301440 | A1 * | 12/2011 | Riley | G16Z 99/00 600/301 |
| 2012/0320080 | A1 | 12/2012 | Giese et al. | |
| 2013/0009993 | A1 * | 1/2013 | Horseman | G06F 19/3418 345/633 |
| 2013/0041290 | A1 * | 2/2013 | Kording | A61B 5/1101 600/595 |
| 2014/0163424 | A1 * | 6/2014 | Kawaguchi | A61B 5/7207 600/595 |
| 2014/0204002 | A1 | 7/2014 | Bennet et al. | |
| 2014/0330159 | A1 * | 11/2014 | Costa | A61B 5/16 600/595 |
| 2015/0017626 | A1 * | 1/2015 | Basson | G09B 7/08 434/353 |
| 2015/0320343 | A1 * | 11/2015 | Utsunomiya | A61B 5/4824 600/595 |
| 2016/0023046 | A1 * | 1/2016 | Evin | A63B 24/0075 482/9 |
| 2016/0077547 | A1 | 3/2016 | Aimone | |
| 2017/0036066 | A1 * | 2/2017 | Chahine | A61B 5/4519 |
| 2017/0095732 | A1 | 4/2017 | Ghaffari et al. | |
| 2017/0156662 | A1 * | 6/2017 | Goodall | A61B 5/7282 |
| 2017/0323485 | A1 * | 11/2017 | Samec | A61B 5/01 |
| 2017/0368413 | A1 * | 12/2017 | Shavit | G06K 9/00342 |
| 2018/0005443 | A1 * | 1/2018 | Poulos | G06F 3/0346 |
| 2018/0133551 | A1 * | 5/2018 | Chang | A63B 24/0075 |
| 2018/0316911 | A1 | 11/2018 | Ishida | |
| 2019/0030394 | A1 * | 1/2019 | Orr | A63B 21/0557 |
| 2019/0307384 | A1 * | 10/2019 | Baeuerle | A61B 5/0533 |
| 2020/0193710 | A1 * | 6/2020 | Talgorn | G06T 19/006 |

FOREIGN PATENT DOCUMENTS

| | | |
|---|---|---|
| JP | 2016122177 A | 7/2016 |
| JP | 6200615 B1 | 9/2017 |
| WO | PCT-2015134953 A1 | 9/2015 |
| WO | 2016124482 A1 | 8/2016 |
| WO | PCT-2017014733 A1 | 1/2017 |
| WO | PCT-2017059215 A1 | 4/2017 |
| WO | 2017085974 A1 | 5/2017 |
| WO | 2019234525 A1 | 12/2019 |

OTHER PUBLICATIONS

International Search Report and Written Opinion, International Application No. PCT/IB2019/053963, dated Sep. 3, 2019, 9 pgs.

"Discover Virtual Reality Beyond Imagination", VIVE™, © 2011-2018 HTC Corporation, 4 pages, <https://www.vive.com/uk/>.

"Myo Gesture Control Armband | Wearable Technology", Thalmic Labs Inc., © 2013-2016, 6 pages, <https://www.myo.com/>.

"PrioVR : Suit up. Game on.", YOST Labs, YouTube, Published Sep. 5, 2013, 1 page, <https://www.youtube.com/watch?v=HnDJXYjFZUg>.

"Reach into virtual reality with your bare hands", Leap Motion, © 2017, Leap Motion, Inc., 7 pages, <https://www.leapmotion.com/#112>.

"tf.nn.sigmoid_cross_entropy_with_logits", TensorFlow, Last updated Mar. 29, 2018, 2 pages, <https://www.tensorflow.org/api_docs/python/tf/nn/sigmoid_cross_entropy_with_logits>.

Arias, et al., "Virtual Reality as a Tool for Evaluation of Repetitive Rhythmic Movements in the Elderly and Parkinson's Disease Patients", PLoS One, Jan. 2012 | vol. 7 | Issue 1, pp. 1-8, <http://journals.plos.org/plosone/article?id=10.1371/journal.pone.0030021>.

Cho, et al., "Detection of Stress Levels from Biosignals Measured in Virtual Reality Environments Using a Kernel-Based Extreme Learning Machine", Sensors, Oct. 2017; 17(10), 16 pages, <https://www.ncbi.nlm.nih.gov/pmc/articles/PMC5677291/>.

Costello, Patrick, "Health and Safety Issues associated with Virtual Reality—A Review of Current Literature", Advanced VR Research Centre, Loughborough University, 23 pages, <http://www.agocg.ac.uk/reports/virtual/37/37.pdf>.

Edison Munoz, et al., "PhysioVR: A Novel Mobile Virtual Reality Framework for Physiological Computing", 2016 IEEE 18th International Conference on e-Health Networking, Applications and Services (Healthcom), 6 pages.

Gibiansky, Andrew, "Speech Recognition with Neural Networks", Wednesday, Apr. 23, 2014, 20 pages, <http://andrew.gibiansky.com/blog/machine-learning/speech-recognition-neural-networks/>.

Kivisto, Joni-Petteri, "Real-Time Muscle Animation", Thesis, Kajaanin Ammattikorkeakoulu University of Applied Sciences, Spring 2012, 43 pages, <https://www.theseus.fi/handle/10024/47903>.

Kopfstein, Janus, "Virtual Reality Allows theMost Detailed, Intimate Digital Surveillance Yet", The Intercept, Dec. 23, 2016, 11 pages, <https://theintercept.com/2016/12/23/virtual-reality-allows-the-most-detailed-intimate-digital-surveillance-yet/>.

Marquez Pedro, et al., "Kinect Evaluation for Human Body Movement Analysis", The Fourth IEEE RAS/EMBS International Conference on Biomedical Robotics and Biomechatronics, Jun. 24-27, 2012, pp. 1856-1861.

Zhang, et al., "Multilabel Neural Networks with Applications to Functional Genomics and Text Categorization", IEEE Transactions on Knowledge and Data Engineering, vol. 18, No. 10, Oct. 2006, pp. 1338-1351.

Notice of Reasons for Refusal (English Translation) dated Aug. 19, 2022 from Japanese Patent Application No. 2020-564486 filed May 14, 2019.

German Patent and Trademark Office, Examination Notice dated Jun. 1, 2023 (translated), DE File No. 11 2019 001 525.7, 12 pages.

* cited by examiner

PHYSIOLOGICAL STRESS OF A USER OF A VIRTUAL REALITY ENVIRONMENT

BACKGROUND

The present disclosure relates to identifying physiological stress of a user of a virtual reality environment.

The provision of virtual reality environments for users to interact with is widely known. Such virtual reality environments, and the devices or systems for providing such environments, are becoming increasing popular, particularly in the field of computer/electronic gaming.

When using such virtual reality environments, it is important that a user takes regular breaks (e.g. to avoid repetitive strain injury, physiological injury, and/or tiredness). This advice can however be overlooked or ignored by users in the field of computer/electronic gaming, especially where users are heavily immersed or engaged within a virtual environment.

Further, in a virtual reality environment, users are often required to interact with virtual objects in three dimensions, at multiple different angles, and/or various orientations relative their current position. This can be difficult and/or stressful for elderly users and physically impaired and/or injured users.

SUMMARY

Disclosed herein are embodiments of a computer-implemented method, a system, and a computer program product for identifying physiological stress of a user of a virtual reality environment. The computer displays to the user a virtual object at an object location within the virtual reality environment and instructs the user to interact with the displayed virtual object. The computer further detects at least one parameter of the user's movement in response to the instruction. The computer determines a measure of physiological stress based on the detected at least one parameter of the user's movement and associates the measure of physiological stress with a part of the user's body based on the object location.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure. It should be understood that the figures are merely schematic and are not drawn to scale.

Figure 1:
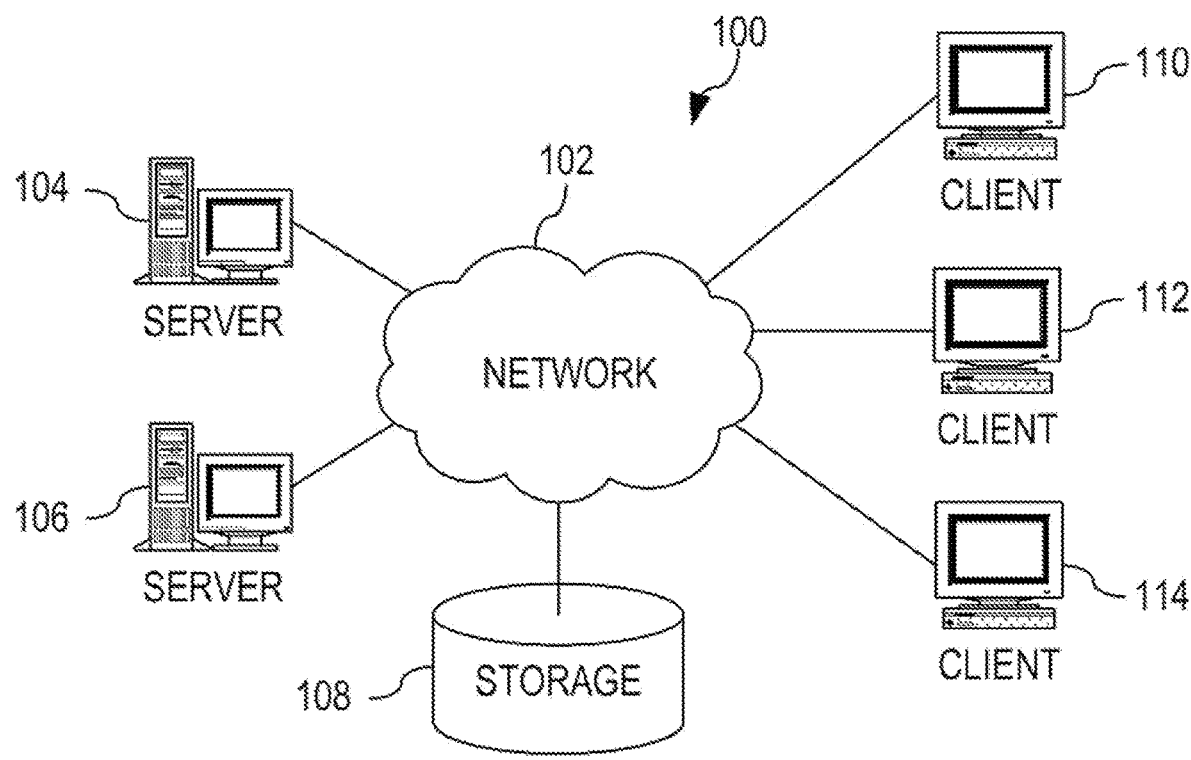
FIG. 1 depicts a block diagram of an example distributed system in which embodiments of the present disclosure may be implemented.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

In the context of the present disclosure, where embodiments of the present disclosure constitute a method, it should be understood that such a method can be a process for execution by a computer, i.e. can be a computer-implementable method. The various steps of the method therefore reflect various parts of a computer program, e.g. various parts of one or more algorithms.

Also, in the context of the present disclosure, a system may be a single device or a collection of distributed devices that are adapted to execute one or more embodiments of the methods of the present disclosure. For instance, a system may be a personal computer (PC), a server, or a collection of PCs and/or servers connected via a network such as a local area network, the Internet, and so on to cooperatively execute at least one embodiment of the methods of the present disclosure.

Disclosed herein is a concept for identifying physiological stress of a user of a virtual reality environment. Embodiments of the present disclosure may utilize the nature and/or characteristics of a user's interaction with a virtual object within a virtual reality so as to provide concepts for identifying areas of the user's body that may be under physiological stress or strain. Proposed approaches to identifying physiological stress or strain of a user's body part are thus enabled due to the context of a user interacting with (e.g. moving or manipulating) a virtual object of a virtual or augmented reality environment. For example, when a user responds to an instruction to interact with a virtual object, one or more aspects of the user's movement in response to the instruction may be detected and used to determine if the user experienced physiological stress as a result of the movement. Embodiments of the present disclosure may therefore provide an approach to dynamically detecting physiological stress on a user's body whilst the user is immersed in a virtual reality environment.

By monitoring body and/or device movements as a user interacts with a virtual object within a virtual or augmented reality environment, information indicative of physiological stress experienced by the user may be obtained. For example, it may be inferred from slow movement of a body part of the user that the body part is under physiological stress or strain. Further, a value of the speed of movement may be directly (or indirectly) correlated to a value of physiological stress experienced.

Embodiments may identify a particular body part that is under physiological stress. Thus, by implementing embodiments of the present disclosure in relation to various different body parts of a user, a stress map of the user's body may be created and/or updated (for example, by associating obtained measures of physiological stress with various body parts of the user). Such information may be maintained in a form that facilitates graphical representation (e.g. graphical map, plot, or chart) of a user's body parts and associated measure(s) of physiological stress.

Embodiments of the present disclosure may take a dynamic and/or targeted approach to detecting physiological stress on a human body using a virtual reality environment. Body and/or device movements may be detected and monitored as a user interacts with the virtual reality environment, and then information about the detected and/or monitored movements may be used to infer one or more measures of physiological stress of the user's body. The obtained measure(s) of stress may then be mapped to one or more body parts to provide body-part-specific physiological information for the user. For example, by considering a reaction time of a user (e.g. the time taken for the user to move a particular body part in response to an instruction), a measure of physiological stress experienced by the user may be inferred. For instance, a slow reaction time (i.e. a large amount of time elapsing before the user moves in response to an instruction) may be indicative of high physiological stress or strain on the moving body part.

By way of example, embodiments may provide for detection of a parameter of the user's movement such as reaction time, speed of movement, or direction of movement. A detected value of a movement parameter may then be compared with a reference value. Based on the result of such a comparison, and in consideration of one or more instructions provided to the user, a measure of physiological stress on a part of the user's body may be determined. Such an approach may thus take account of a relationship between the current movement of the user and a reference value of movement (such as a previous, recent, or preceding detected movement).

In some embodiments, the reference value may be associated with the virtual object, the object location, and/or the user. The process of determining physiological stress may thus be tailored to specifics of the user, the virtual environment, and/or the virtual object so as to provide more accurate and/or more relevant results.

It will, however, be appreciated that the process of determining a measure of physiological stress based on a detected at parameter of user movement may be adjusted or configurable by a user, for example.

In some embodiments, a reference value employed by the determination process may be adjusted or configurable by a user for example. By way of example, in some embodiments, a reference value may be modified based on a determined measure of physiological stress. In this way, a reference value may be adjusted or updated to reflect a newly determined measure of physiological stress, so as to provide a more accurate or relevant value for comparison/assessment purposes.

Some embodiments may further comprise detecting an audio or visual cue of the user in response to the instruction. Determining a measure of physiological stress may then be further based on the detected audio or visual cue. In this way, embodiments may utilize other sensory inputs and information to provide a more detailed and accurate determination of physiological stress. For example, detection of pain-indicating gasps, grunts, or other audio clues may be leveraged to provide additional information for determining a measure of physiological stress. Detection of specific spoken words or phrases (such as "ouch" or "that hurts" for example) may indicate stress or pain when moving a particular body part. In some embodiments, a silence from a user (such as a user engaged in conversation who ceases talking) may be used as an audio cue that the user has some physiological stress and is concentrating on the task. Detection of such sounds may employ known voice recognition techniques, and/or a neural network system adapted to detect and identify particular sounds or spoken words. Such approaches may provide a more detailed and accurate determination of a measure of physiological stress.

Embodiments may further comprise determining a target part of the user's body for which to identify a measure of physiological stress. Displaying to the user a virtual object at an object location within the virtual reality environment may then be based on the target part of the user's body. Further, associating the measure of physiological stress with a part of the user's body may then comprise associating the measure of physiological stress with the target part of the user's body. Dynamic and targeted assessment of physiological stress of different body parts may thus be facilitated. For instance, a stress map of a user's body may be created by probing different body parts via various instructions to the user (e.g. to identify difficult or hard to reach areas/locations for the user). This may be done by manipulating the virtual reality environment in order to gain physiological stress information about specific areas or parts of a user's body. Such manipulation of the virtual reality environment may then be mapped to movements of the user (e.g. speed, reaction times, movement direction, etc.).

Accordingly, it will be appreciated that various embodiments may enable the adaptation of a virtual reality environment to cater for different areas/region of physiological stress that may be experienced by a user. Embodiments may be adapted to target specific areas or parts of a user's body, so as to avoid or reduce physiological stress on a body part and/or provide rehabilitation or treatment to a body part. For example, based on a determined measure of physiological stress for a user, placement of a virtual object in a virtual reality environment may be adapted to reduce or minimize of physiological stress for the user when he/she interacts with the virtual object.

Some embodiments may provide for adaptation and/or manipulation of a virtual reality environment to identify different areas of physiological stress. Embodiments may, for instance, target specific areas of a user's body so as to obtain information specific to one or more body parts.

In some embodiments, determining a target part of the user's body may comprise identifying a part of the user's body not having an associated measure of physiological stress. In this way, more complete or relevant information regarding physiological stress may be obtained. For example, unnecessary repetition of obtaining information for the same body part may be avoided, and resources may instead be adapted to obtain physiological information that is lacking or missing for a user (e.g. missing from stress map for user).

Some embodiments may further comprise obtaining historical information relating to a previously determined measure of physiological stress. Determining a measure of physiological stress may then be further based on the obtained historical information. In this way, embodiments may utilize other previously obtained measurements and information to provide a more detailed and accurate determination of physiological stress.

For determining a measure of physiological stress based on a detected parameter of the user's movement, many different approaches may be employed. However, in some embodiments, a measure of physiological stress may be determined by analyzing a detected movement parameter such as speed, reaction time, and/or movement direction, and such analysis can be based on one or more specific characteristics of how the user moves in response to an instruction to interact with a displayed virtual object. Thus, in some embodiments, one or more factors of how a user engages with a virtual object can be used to determine a measure of physiological stress experienced by the user.

By way of further example, some embodiments may provide extensions to a virtual reality system. Such extensions may provide for effective (e.g., more relevant) user treatment to be provided. In this way, a user may not be excessively stressed or inappropriately treated as a result of incorrectly or poorly targeted instructions. For example, embodiments may be employed to target specific areas of a user's body for virtual treatment methods or to avoid positioning virtual objects at locations in a virtual environment which are difficult or stressful to reach.

Illustrative embodiments may therefore provide concepts for controlling the provision of instructions, physiological treatment, and/or virtual object(s) to a user of a virtual/augmented reality system. Dynamic virtual/augmented reality control concepts may therefore be provided by some embodiments of the present disclosure.

Modifications and additional steps to a traditional virtual/augmented reality system may also be proposed which may enhance the value and utility of the proposed concepts.

Figure 2:
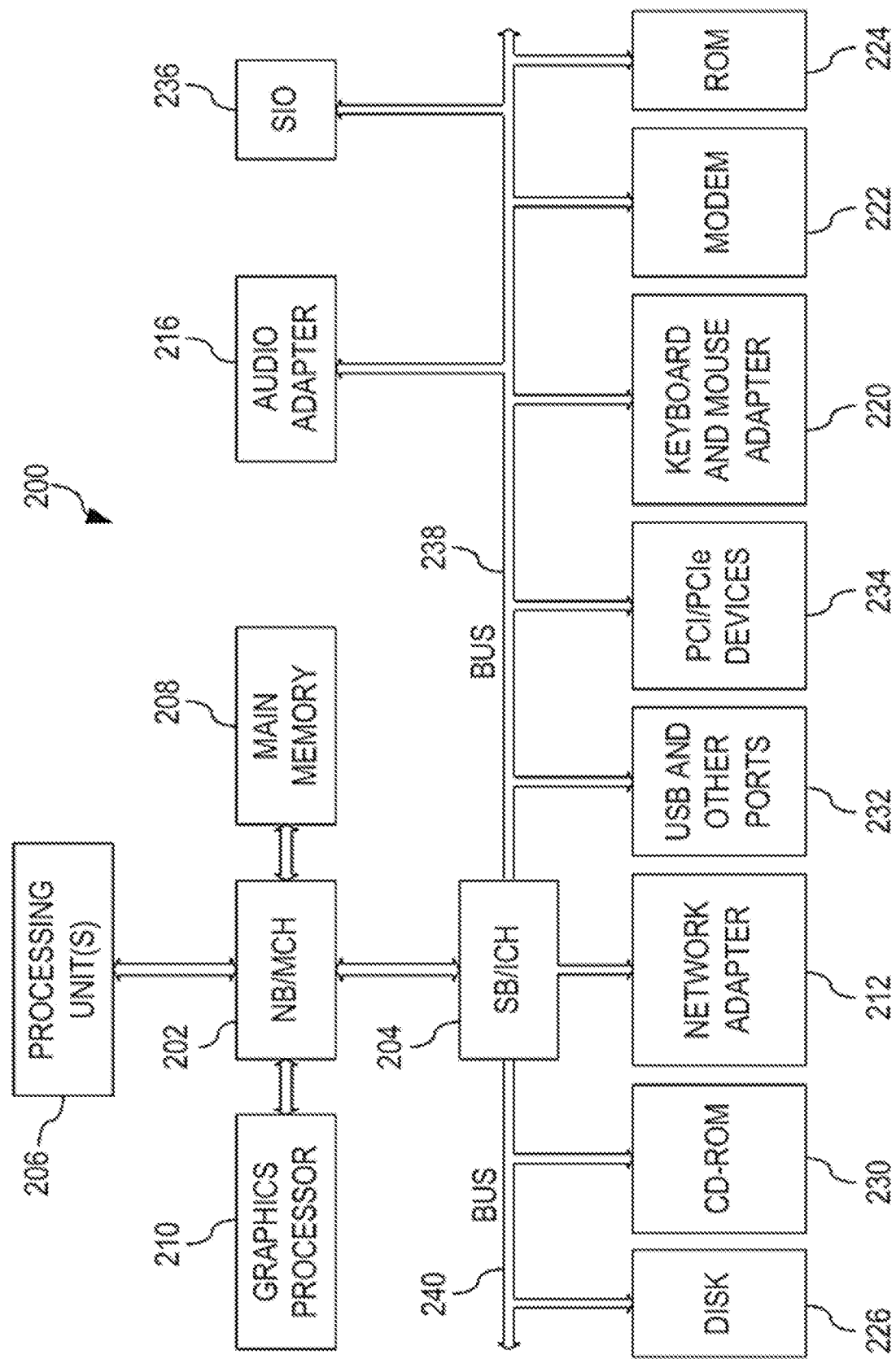
FIG. 2 is a block diagram of an example system in which embodiments of the present disclosure may be implemented.

Illustrative embodiments may be utilized in many different types of virtual or augmented reality environments. In order to provide a context for the description of elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present disclosure may be implemented. Many modifications to the depicted environments may be made without departing from the scope of the present disclosure.

FIG. 1 depicts a block diagram of an example distributed system in which embodiments of the present disclosure may be implemented. Distributed system 100 may include a network of computers in which aspects of the illustrative embodiments may be implemented. The distributed system 100 contains at least one network 102, which is the medium used to provide communication links between various devices and computers connected together within the distributed data processing system 100. The network 102 may include connections, such as wire, wireless communication links, or fiber optic cables.

In the depicted example, a first server 104 and second server 106 are connected to the network 102 along with a storage unit 108. In addition, clients 110, 112, and 114 are also connected to the network 102. The clients 110, 112, and 114 may be, for example, personal computers, network computers, or the like. In the depicted example, the first server 104 can provide data, such as boot files, operating system images, and applications to the clients 110, 112, and 114. Clients 110, 112, and 114 are clients to the first server 104 in the depicted example. The distributed system 100 may include additional servers, clients, and other devices not shown.

In the depicted example, the distributed system 100 can be a subset of the Internet with the network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational, and other computer systems that route data and messages. The distributed system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present disclosure, and therefore, the particular elements shown in FIG. 1 should not be considered limiting with regard to the environments in which the illustrative embodiments of the present disclosure may be implemented.

FIG. 2 is a block diagram of an example system 200 in which embodiments of the present disclosure may be implemented. The system 200 is an example of a computer, such as client 110 in FIG. 1, or server 104 in FIG. 1, in which computer usable code or instructions implementing the processes for illustrative embodiments of the present disclosure can be located.

In the depicted example, the system 200 employs a hub architecture including a north bridge and memory controller hub (NB/MCH) 202 and a south bridge and input/output (I/O) controller hub (SB/ICH) 204. One or more processing units 206, a main memory 208, and a graphics processor 210 are connected to NB/MCH 202. The graphics processor 210 may be connected to the NB/MCH 202 using, for example, Peripheral Component Interconnect Express (PCIe) or through an accelerated graphics port (AGP).

In the depicted example, a network adapter 212 (which can be a local area network (LAN) adapter) connects to SB/ICH 204. An audio adapter 216, a keyboard and a mouse adapter 220, a modem 222, a read only memory (ROM) 224, a hard disk drive (HDD) 226, a CD-ROM drive 230, one or more universal serial bus (USB) ports and other communication ports 232, and PCI/PCIe devices 234 connect to the SB/ICH 204 through first bus 238 and second bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

The HDD 226 and CD-ROM drive 230 connect to the SB/ICH 204 through second bus 240. The HDD 226 and CD-ROM drive 230 may use, for example, an integrated drive electronics (IDE) or a serial advanced technology attachment (SATA) interface. Super I/O (SIO) device 236 may be connected to SB/ICH 204.

An operating system runs on the one or more processing unit(s) 206. The operating system can coordinate and provide control of various components within the system 200 in FIG. 2. As a client, the operating system may be a commercially available operating system. An object-oriented programming system, such as the Java™ programming system, may run in conjunction with the operating system and provides calls to the operating system from Java™ programs or applications executing on system 200.

As a server, system 200 may be, for example, an IBM® eServer™ System p® computer system, running the Advanced Interactive Executive (AIX®) operating system or the LINUX® operating system. The system 200 may be a symmetric multiprocessor (SMP) system including a plurality of processors in processing unit 206. Alternatively, a single processor system may be employed.

Instructions for the operating system, the programming system, and applications or programs can be located on storage devices, such as HDD 226, and may be loaded into main memory 208 for execution by one or more processing unit(s) 206. Similarly, one or more message processing programs according to an embodiment may be adapted to be stored by the storage devices and/or the main memory 208.

The processes for illustrative embodiments of the present disclosure may be performed by one or more processing unit(s) 206 using computer usable program code, which may be located in a memory such as, for example, main memory 208, ROM 224, or in one or more peripheral devices, including HDD 226 and CD-ROM drive 230.

A bus system, such as first bus 238 or second bus 240 as shown in FIG. 2, may comprise one or more buses. The bus system may be implemented using any type of communication fabric or architecture that provides for a transfer of data between different components or devices attached to the fabric or architecture. A communication unit, such as the modem 222 or the network adapter 212 of FIG. 2, may include one or more devices used to transmit and receive data. A memory may be, for example, main memory 208, ROM 224, or a cache such as found in NB/MCH 202 in FIG. 2.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the system mentioned previously, without departing from the spirit and scope of the present disclosure.

Moreover, the system 200 may take the form of any of a number of different data processing systems including client computing devices, server computing devices, a tablet computer, laptop computer, a telephone or other communication device, a personal digital assistant (PDA), or the like. In some illustrative examples, the system 200 may be a portable computing device that is configured with flash memory to provide non-volatile memory for storing operating system files and/or user-generated data, for example. Thus, the system 200 may essentially be any known or later-developed data processing system without architectural limitation.

As detailed above, embodiments of the present disclosure include a method for identifying physiological stress of a user of a virtual reality environment. Such a method can comprise instructing the user to interact with a virtual object within a virtual reality environment. The method can then comprise detecting at least one parameter of the user's movement in response to the instruction. Based on the detected parameter(s) of the user's movement, a measure of physiological stress may be determined. Proposed embodiments may thus be employed to determine when a user is under physiological stress or strain as a result of interacting with a virtual reality environment. This may then be further used to adapt the virtual reality environment and/or instructions so as to avoid or prevent a user experiencing physiological stress or strain.

Accordingly, by way of explanation, described below is a method for identifying physiological stress of a user of a virtual reality environment according to some embodiments. As mentioned above, many different approaches to determining a measure of physiological stress based on detected user interaction with a virtual object may be employed. By way of example, and with reference to FIG. 3, there is depicted a flow diagram of a method 300 for identifying physiological stress of a user of a virtual reality environment. Here, the virtual reality environment is adapted to provision of virtual objects for a user to interact with.

The method begins at 310 by displaying to the user one or more virtual objects at one or more object locations within the virtual reality environment. This may, for example, be implemented using a conventional virtual reality system having a controller and a head-mounted display unit.

Next, at 320, the user is instructed to interact with one or more of the displayed virtual object(s). Such instruction may, for example, be provided using an audio and/or visual prompt indicating a virtual object and an action to be performed with the virtual object. However, it will be appreciated that the instruction may comprise any suitable form of prompt to the user that instructs the user to interact with the virtual environment. It may, for instance, instruct the user to choose a menu item or complete a certain move/action within the virtual environment, game, or application. In embodiments where more than one virtual object is displayed, the instruction can relate to one of the virtual objects or can involve more than one virtual objects (such as an instruction to make the virtual objects interact). The prompt may be delivered via a visual and/or audible cue and/or via a tactile interface (e.g. as vibrations of a handheld controller).

An additional possibility relates to virtual reality applications that interface with the real world. Here, real world prompts could be employed. For example, a virtual reality application could be developed that allows a user to turn lights off in the virtual world, that links to the real lights in the room in the real world. An audio prompt could be delivered from the real world to prompt the user to perform an action in the virtual world.

One or more parameters of the user's movement in response to the instruction are then detected at 330. By way of example, the detected parameter(s) of the user's movement may comprise reaction time, speed of movement, or direction of movement. For this purpose, a tracking component may be employed which is adapted to track controller movements, head-mounted display unit movements, and body movements of the user. For such movement tracking, a direction, speed, and length of movement (and/or any other aspect of movement) may be sensed and monitored. This monitoring can be continuous or may involve a series of data points.

By way of example, controller and headset movements can be tracked using existing virtual reality technology that is widely available in existing virtual/augmented reality systems and devices. Body movements may be inferred from controller and/or headset movements and/or optical recognition systems that are widely available (for example, in video games consoles and accessories). The illustrated embodiment may therefore leverage existing movement sensing and tracking technologies, and may further integrate multiple different approaches.

Operation 330 may also comprise detecting and monitoring reaction times and/or identifying which body part(s) move, in addition to the above described parameters.

Then, at 340, a measure of physiological stress is determined based on the detected parameter(s) of the user's movement. In some embodiments, operation 340 of determining comprises comparing the detected parameter of the user's movement against a reference value, wherein the reference value may be associated with at least one of: one or more virtual objects, one or more virtual object's locations, and the user. For example, by comparing a detected speed of movement of the user against a reference speed value, a measure of physiological stress experienced by the user may be determined. For instance, a speed value being lower than a reference speed value may be indicative of high physiological stress or strain on the user.

Then, based on the result of such a comparison, and in consideration of the instruction provided to the user, a measure of physiological stress on a part of the user's body may be determined. Such an approach may thus take into account a relationship between the detected movement of the user and a reference value of movement (such as an average speed value for a population of users, for example).

By way of further example, operation 340 can further comprise analyzing detected movement speed, patterns, directions, etc. to infer shaky, strained, or unusual movements made by the user. Such analysis may include comparing the detected movement speed, patterns, directions, etc. against pre-existing reference data. Additionally, or alternatively, biometric data may be obtained and analyzed to infer a measure of physiological stress. Such biometric data may, for example, be obtained through connection to a wearable sensor (e.g. a heart rate sensor, blood pressure monitor, etc.) and/or through what is observed from the headset or controller (e.g. skin temperature).

By way of further example, some embodiments of the present disclosure may comprise additional steps (as indicated by the dashed boxes of FIG. 3) which may further improve the accuracy and/or usefulness of a determined measure of physiological stress.

In particular, the method 300 may further comprise in 350 obtaining historical information relating to a previously determined measure of physiological stress. The step 340 of determining a measure of physiological stress may then be further based on the obtained historical information. For instance, obtained historical information may be used to check or qualify a determined measure of physiological stress, thereby catering for erroneous or outlying values. Further, use of predetermined measures of physiological stress may enable embodiments to provide a comparison of how the user is performing against a previous situation or a baseline "normal" measure. This may employ a comparison of the newly-obtained measure against the historical data. A result of the comparison may then be communicated to the user (e.g. "We notice that your left arm appears more stressed than what it is normally expected for a user of your height, weight, age, etc."). Additionally, or alternatively, historical data regarding the user's physiological stress information may be to show progress or improvements for body parts. This may be useful for rehabilitation applications.

Also, by way of further example, the method may further comprise operation 360 of detecting an audio or visual cue of the user in response to the instruction. The step 340 of determining a measure of physiological stress may then be further based on the detected audio or visual cue. In this way, such embodiments may obtain other sensory inputs, beyond the detected parameter(s) of user movement at 330, and supplementary indicators that may be used to provide a more detailed and accurate determination of physiological stress. For example, audible and/or visible clues may be leveraged to provide additional information for determining (or qualifying) a measure of physiological stress. Detection of specific spoken words or phrases (such as "ouch" or "that hurts" for example) and/or visual cues (such as a user wincing in pain) exhibited by the user may indicate stress or pain when moving a particular body part. Detection of such sounds or sights may employ known voice and/or visual feature recognition techniques and/or systems.

Furthermore, some embodiments may further comprise operation 370 of associating the determined measure of physiological stress with a part of the user's body and this may, for example, be done based on one or more objects' location(s).

For example, when a user responds to an instruction to interact with a virtual object at a specific object location, one or more aspect of the user's movement in response to the instruction may be detected and used to determine if and what body part are under physiological stress. The determined measure of stress may then be mapped to one or more body parts to provide body-part-specific physiological information for the user.

Yet further, a proposed method may further comprise determining a target part of the user's body (e.g. a body part for which a measure of physiological stress is missing or required). At 310, the displaying to the user of one or more virtual objects at one or more object locations within the virtual reality environment may then be based on the target part of the user's body. In this way, targeted assessment of physiological stress of different body parts may thus be facilitated. Also, a stress map of a user's body may be created by probing different body parts via various instructions to the user (e.g. to identify difficult or hard to reach areas/locations for the user).

It should therefore be appreciated that proposed embodiments of the present disclosure may be employed in combination with a process of manipulating the virtual reality environment in order to gain physiological stress information about specific areas or parts of a user's body. Such manipulation of the virtual reality environment may then be mapped to movements of the user (e.g. speed, reaction times, movement direction, etc.) in order to determine a measure of physiological stress for the specific areas or parts of the user's body.

Using information regarding a determined measure of stress for each body part, a map may be generated which identifies areas/parts of a user's body which may have difficulty in accessing objects in one or more particular positions in a virtual reality environment. For example, if a user has a stiff left shoulder, he/she may find it difficult to reach for objects that are located on their left-side at an elevation relative to his/her forward stance. A measure of physiological stress obtained using method 300 may identify this by inferring from movement data that objects placed high and to the left take a relatively longer time to interact with and/or are moved more slowly than objects placed at other relative positioning. A map may be generated by averaging such reaction times and/or movement speeds for each body part.

For areas/portions of the map having no associated physiological stress measure(s), the virtual/augmented reality environment may be adapted and/or interaction instructions provided to the user so as to enable capture of required movement data. For instance, virtual objects may be strategically positioned in the virtual/augmented reality environment so that as user must interact with them using one or more particular target body parts (e.g. body parts for which a measure of physiological stress is to be determined). Resultant movement speed, direction, patterns, etc. may then be analyzed to determine a measure of physiological stress for the target body part(s). In some embodiments, it may also be identified that a user refuses/declines to use a target body part. This can occur at 330 and detection of one or more parameters of user movement can entail detecting a lack of movement; this may be indicative of significant physiological stress to the target body part.

From the above description, it will be appreciated that there is proposed a concept of detecting one or more characteristics of a user's interaction with a virtual object within a virtual reality environment as a way of determining a measure of physiological stress experienced by the user.

This can be implemented on a part-by-part basis, and/or utilized across multiple body parts simultaneously. For instance, information from detected movements when interacting with multiple virtual objects may be used to determine different measures of physiological stress for different body parts of the user.

From the description provided above, it will be understood that proposed embodiments may utilize the nature and/or characteristics of user movement when interacting with a virtual object within a virtual or augmented virtual environment so as to provide concepts for determining a measure of physiological stress experienced by the user. This may allow for highly efficient instruction and/or treatment of user of a virtual reality environment, since the provision of virtual objects and/or instructions may be controlled based on a determined physiological stress for the user and consideration of whether activity of the user in the virtual reality environment may result in an undesirable/unacceptable physiological stress for the user.

Embodiments may therefore be provided as extensions to existing virtual reality systems. Such extensions may provide for targeted (e.g. less stressful or more convenient) virtual objects and/or user notifications to be provided. In this way, a user may not be provided with virtual objects and/or instruction that cause unnecessary or excessive physiological stress to the user.

Figure 3:
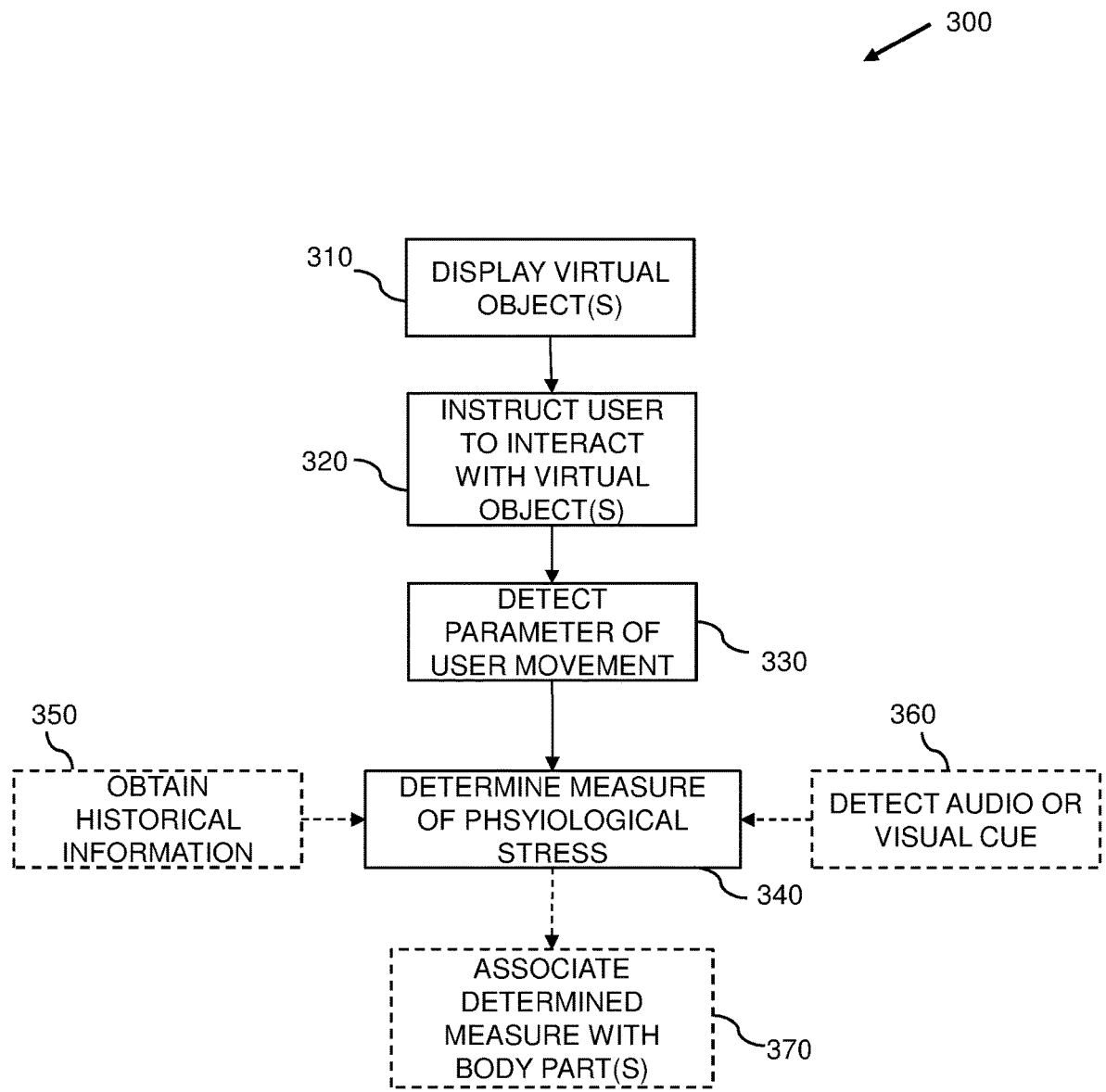
FIG. 3 is a flow diagram of a method for identifying physiological stress of a user of a virtual reality environment, in accordance with embodiments of the present disclosure.

In some embodiments, there may be provided a system comprising a processing arrangement adapted to carry out any method previously described with reference to FIGS. 1 to 3.

Figure 4:
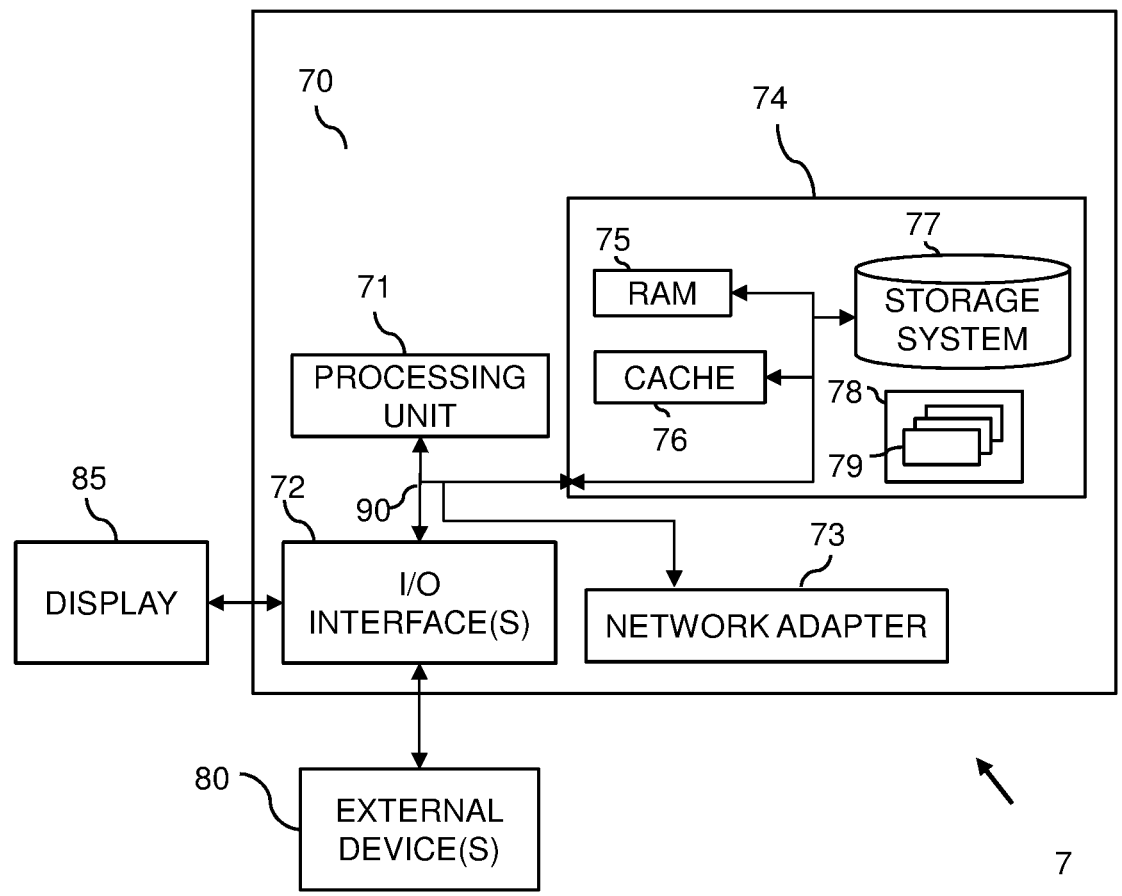
FIG. 4 illustrates a system for identifying physiological stress of a user of a virtual reality environment according to an embodiment.

By way of example, as illustrated in FIG. 4, embodiments may comprise a computer system 70, which may form part of a networked system 7. The components of computer system 70 may include, but are not limited to, one or more processing arrangements, for example comprising processors or processing units 71, a system memory 74, and a bus 90 that couples various system components including system memory 74 to processing unit 71.

Bus 90 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system 70 typically includes a variety of computer system readable media. Such media may be any available media that is accessible by computer system 70, and it includes both volatile and non-volatile media, removable and non-removable media.

System memory 74 can include computer system readable media in the form of volatile memory, such as random access memory (RAM) 75 and/or cache memory 76.

Computer system 70 may further include other removable/non-removable, volatile/non-volatile computer system storage media. By way of example only, storage system 77 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 90 by one or more data media interfaces. As will be further depicted and described below, memory 74 may include at least one program product having a set (e.g., at least one) of program modules that are configured to carry out the functions of embodiments of the disclosure.

Program/utility 78, having a set (at least one) of program modules 79, may be stored in memory 74 by way of example, and not limitation, as well as an operating system, one or more application programs, other program modules, and program data. Each of the operating system, one or more application programs, other program modules, and program data or some combination thereof, may include an implementation of a networking environment. Program modules 79 generally carry out the functions and/or methodologies of embodiments of the disclosure as described herein.

Computer system 70 may also communicate with one or more external devices 80 such as a keyboard, a pointing device, a display 85, etc.; one or more devices that enable a user to interact with computer system 70; and/or any devices (e.g., network card, modem, etc.) that enable computer system 70 to communicate with one or more other computing devices. Such communication can occur via Input/Output (I/O) interfaces 72. Still yet, computer system 70 can communicate with one or more networks such as a local area network (LAN), a general wide area network (WAN), and/or a public network (e.g., the Internet) via network adapter 73. As depicted, network adapter 73 communicates with the other components of computer system 70 via bus 90. It should be understood that although not shown, other hardware and/or software components could be used in conjunction with computer system 70. Examples, include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention are being presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for reducing physiological stress of a user of a virtual reality environment, the method comprising:
   displaying to the user a plurality of virtual objects at a plurality of object locations within the virtual reality environment;
   continuously detecting a plurality of parameters of movement of the user in response to the plurality of virtual objects, wherein the detected plurality of parameters of movement of the user comprise a reaction time, a speed of movement, and a direction of movement;
   continuously detecting spoken words from the user in response to the display of the plurality of virtual objects;
   continuously detecting visual cues of the user in response to the display of the plurality of virtual objects;
   determining a plurality of measures of physiological stress based on:
      a change in the detected plurality of parameters of movement of the user from a plurality of previously-detected parameters of movement by the user;
      a comparison of the detected plurality of parameters of movement with one or more additional users of the virtual reality environment;

the detected spoken words; and
the detected visual cues;
associating the plurality of measures of physiological stress with one or more of a plurality of parts of a user's body based on the respective object locations of the plurality of virtual objects to create a body-part-specific mapping for the user,
wherein the body-part-specific mapping includes a plurality of different body parts; and
proactively adapting the virtual reality environment based on the plurality of measures of physiological stress and the body-part-specific mapping to reduce physiological stress on specific ones or more of the plurality of different body parts based on the body-part-specific mapping for the user, wherein the proactive adaptions comprise changing the object location of one or more of the plurality of virtual objects to an adapted object location that reduces physiological stress on one or more of the plurality of parts of the user's body.

2. The method of claim 1, further comprising instructing the user to interact with the displayed plurality of virtual objects, wherein adapting the virtual reality environment is performed for rehabilitation or treatment of the one or more of a plurality of parts of the user's body.

3. The method of claim 1, further comprising:
determining a target part of the user's body for which at least one of the plurality of measures of physiological stress is to be determined;
adding the plurality of measures of physiological stress to a graphical map of the user's body parts;
wherein the displaying to the user the plurality of virtual objects at the plurality of object locations within the virtual reality environment is based on the target part of the user's body,
and wherein the associating the plurality of measures of physiological stress with the one or more parts of the user's body comprises associating the at least one of the plurality of measures of physiological stress with the target part of the user's body.

4. A non-transitory computer program product for reducing physiological stress of a user of a virtual reality environment, the computer program product comprising a computer readable storage medium having program instructions embodied therewith, wherein the computer readable storage medium is not a transitory signal per se, the program instructions executable by a computer system to perform a method comprising:
displaying to the user a plurality of virtual objects at a plurality of object locations within the virtual reality environment;
continuously detecting a plurality of parameters of movement of the user in response to the plurality of virtual objects, wherein the detected plurality of parameters of movement of the user comprise a reaction time, a speed of movement, and a direction of movement;
continuously detecting spoken words from the user in response to the display of the plurality of virtual objects;
continuously detecting visual cues of the user in response to the display of the plurality of virtual objects;
determining a plurality of measures of physiological stress based on:
a change in the detected plurality of parameters of movement of the user from a plurality of previously-detected parameters of movement by the user;
a comparison of the detected plurality of parameters of movement with one or more additional users of the virtual reality environment;
the detected spoken words; and
the detected visual cues;
associating the plurality of measures of physiological stress with one or more of a plurality of parts of a user's body based on the respective object locations of the plurality of virtual objects to create a body-part-specific mapping for the user,
wherein the body-part-specific mapping includes a plurality of different body parts; and
proactively adapting the virtual reality environment based on the plurality of measures of physiological stress and the body-part-specific mapping to reduce physiological stress on specific ones or more of the plurality of different body parts based on the body-part-specific mapping for the user, wherein the proactive adaptions comprise changing the object location of one or more of the plurality of virtual objects to an adapted object location that reduces physiological stress on one or more of the plurality of parts of the user's body.

5. The computer program product of claim 4, wherein the method further comprises:
determining a target part of the user's body for which at least one of the plurality of measures of physiological stress is to be determined;
adding the plurality of measures of physiological stress to a graphical map of the user's body parts;
wherein the displaying to the user the plurality of virtual objects at the plurality of object locations within the virtual reality environment is based on the target part of the user's body, and
wherein the associating the plurality of measures of physiological stress with the one or more parts of the user's body comprises associating the at least one of the plurality of measures of physiological stress with the target part of the user's body.

6. A system for reducing physiological stress of a user of a virtual reality environment, the system comprising:
one or more processors; and
a memory communicatively coupled to the one or more processors,
wherein the memory comprises instructions which, when executed by the one or more processors, cause the one or more processors to perform a method comprising:
displaying to the user a plurality of virtual objects at a plurality of object locations within the virtual reality environment;
continuously detecting a plurality of parameters of movement of the user in response to the plurality of virtual objects,
wherein the detected plurality of parameters of movement of the user comprise a reaction time, a speed of movement, and a direction of movement;
continuously detecting spoken words from the user in response to the display of the plurality of virtual objects;
continuously detecting visual cues of the user in response to the display of the plurality of virtual objects;
determining a plurality of measures of physiological stress based on:
a change in the detected plurality of parameters of movement of the user from a plurality of previously-detected parameters of movement by the user;

a comparison of the detected plurality of parameters of movement with one or more additional users of the virtual reality environment;
the detected spoken words; and
the detected visual cues;
associating the plurality of measures of physiological stress with one or more of a plurality of parts of a user's body based on the respective object locations of the plurality of virtual objects to create a body-part-specific mapping for the user, wherein the body-part-specific mapping includes a plurality of different body parts; and
proactively adapting the virtual reality environment based on the plurality of measures of physiological stress and the body-part-specific mapping to reduce physiological stress on specific ones or more of the plurality of different body parts based on the body-part-specific mapping for the user,
wherein the proactive adaptions comprise changing the object location of one or more of the plurality of virtual objects to an adapted object location that reduces physiological stress on one or more of the plurality of parts of the user's body.

7. The system of claim 6, wherein the one or more processors are configured for:

determining a target part of the user's body for which at least one of the plurality of measures of physiological stress is to be determined;
adding the plurality of measures of physiological stress to a graphical map of the user's body parts;
wherein the displaying to the user the plurality of virtual objects at the plurality of object locations within the virtual reality environment is based on the target part of the user's body,
and wherein the associating the plurality of measures of physiological stress with the one or more parts of the user's body comprises associating the at least one of the plurality of measures of physiological stress with the target part of the user's body.

8. The system of claim 6, wherein the one or more processors are configured to:

obtain historical information relating to a previously determined at least one of the plurality of measures of physiological stress,
and wherein determining the plurality of measures of physiological stress is further based on the obtained historical information.

\* \* \* \* \*